(12) United States Patent
Goel et al.

(10) Patent No.: US 11,326,417 B2
(45) Date of Patent: May 10, 2022

(54) ANALYZING MIXABILITY OF WELL CEMENT SLURRIES

(71) Applicant: Halliburton Energy Services, Inc., Houston, TX (US)

(72) Inventors: Vivek S. Goel, Humble, TX (US); Pauline Akinyi Otieno, Spring, TX (US); Xueyu Pang, Houston, TX (US); Thomas Singh Sodhi, New Caney, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 225 days.

(21) Appl. No.: 16/552,565

(22) Filed: Aug. 27, 2019

(65) Prior Publication Data

US 2019/0383116 A1 Dec. 19, 2019

Related U.S. Application Data

(62) Division of application No. 15/324,469, filed as application No. PCT/US2014/053245 on Aug. 28, 2014, now Pat. No. 10,450,830.

(51) Int. Cl.
| | |
|---|---|
| *E21B 33/16* | (2006.01) |
| *C09K 8/42* | (2006.01) |
| *B28C 7/02* | (2006.01) |
| *C04B 28/02* | (2006.01) |
| *C04B 40/00* | (2006.01) |
| *G01N 33/38* | (2006.01) |

(52) U.S. Cl.
CPC .............. *E21B 33/16* (2013.01); *B28C 7/024* (2013.01); *B28C 7/026* (2013.01); *C04B 28/02* (2013.01); *C04B 40/0032* (2013.01); *C09K 8/42* (2013.01); *G01N 33/388* (2013.01)

(58) Field of Classification Search
CPC ........................................................ E21B 33/16
See application file for complete search history.

(56) References Cited

U.S. PATENT DOCUMENTS

| | | | |
|---|---|---|---|
| 4,594,883 A * | 6/1986 | Pollard | ............. B01F 15/00201 |
| | | | 73/54.23 |
| 6,258,757 B1 | 7/2001 | Sweatman et al. | |
| 8,511,381 B2 | 8/2013 | Panga et al. | |

(Continued)

FOREIGN PATENT DOCUMENTS

WO 2016032498 A1 3/2016

*Primary Examiner* — Anshu Bhatia
(74) *Attorney, Agent, or Firm* — Thomas Rooney; Parker Justiss, P.C.

(57) ABSTRACT

Some aspects of what is described here relate to analyzing a well cement slurry. In some aspects, a well cement slurry is mixed in a mixer under a plurality of conditions. The plurality of conditions correspond to a plurality of distinct Reynolds number values for the well cement slurry in the mixer. Power number values associated with mixing the well cement slurry in the mixer under the plurality of conditions are identified. Each power number value is based on an amount of energy used to mix the well cement slurry under a respective one of the plurality of conditions. Values for parameters of a functional relationship between power number and Reynolds number are identified based on the power number values and the Reynolds number values for the plurality of conditions.

10 Claims, 4 Drawing Sheets

(56) References Cited

U.S. PATENT DOCUMENTS

| | | |
|---|---|---|
| 2008/0147367 A1 | 6/2008 | Massingill et al. |
| 2010/0212892 A1 | 8/2010 | Santra et al. |
| 2011/0127034 A1 | 6/2011 | Vidick et al. |
| 2016/0271834 A1 | 9/2016 | Sodhi et al. |

* cited by examiner

ANALYZING MIXABILITY OF WELL CEMENT SLURRIES

CROSS-REFERENCE TO RELATED APPLICATION

This application is a divisional of U.S. patent application Ser. No. 15/324,469, entitled "ANALYZING MIXABILITY OF WELL CEMENT SLURRIES," filed on Jan. 6, 2017, which was a National Stage of International Application No. PCT/US2014/053245 filed on Aug. 28, 2014, entitled, "ANALYZING MIXABILITY OF WELL CEMENT SLURRIES," which was published in English under International Publication Number WO 2016/032498 on Mar. 3, 2016. The above application is commonly assigned with this National Stage application and is incorporated herein by reference in its entirety.

BACKGROUND

The following description relates to analyzing mixability of well system fluids, including well cement slurries and other types of well system fluids.

Cement compositions may be used in a variety of subterranean operations, such as, in the production and exploration of hydrocarbons, e.g., oil, gas, and other hydrocarbons, onshore and offshore. For example, a subterranean well can be constructed using a pipe string (e.g., casing, liners, expandable tubulars, etc.), which can be run into a wellbore and cemented in place. The process of cementing the pipe string in place is commonly referred to as "primary cementing." In a typical primary cementing method, a cement composition is pumped into an annulus between the wellbore and the exterior surface of the pipe string disposed therein. The cement composition can set in the annular space, thereby forming an annular sheath of hardened, substantially impermeable cement (i.e., a cement sheath). The cement sheath can support and position the pipe string in the wellbore and bond the exterior surface of the pipe string to the subterranean formation. The cement sheath surrounding the pipe string functions to prevent the migration of fluids in the annulus among other things, and to protect the pipe string from corrosion.

A broad variety of well cement compositions have been used in subterranean well cementing operations. Such well cement compositions can be made, for example, by mixing portland cement with water and often with one or more other additives such as retarders, accelerators, and lightweight additives. The additives can be either dry powder, liquid or both. The components are mixed under certain mixing conditions (e.g., mixing speeds, mixing times, and other conditions). For example, industry guideline specifications for laboratory experiments designed to mimic field operations, which include quantities and mixing conditions, for mixing a specified volume of a cement composition are provided, e.g., by institutions such as the American Petroleum Institute (API) or other institutions.

DESCRIPTION OF DRAWINGS

Like reference symbols in the various drawings indicate like elements.

DETAILED DESCRIPTION

In some implementations of what is described here, an algorithm is used to determine the mechanical energy to mix a well system fluid, for example, at the lab scale or in the field. With knowledge of the energy requirements, a comparison of the predicted energy requirements with previously-mixed "easy to mix" and "hard to mix" slurries can be made, and a slurry can hence be classified according to an objective or quantitative "mixability index." In some instances, the algorithm saves time, labor and money when dealing with difficult to mix slurries.

The American Petroleum Institute (API) recommends the industry guideline standard for mixing well cement slurries in the lab, and it recommends specifications for mixing a specific volume of neat well cement slurries at certain speeds for certain periods of time. When additives are incorporated into the well cement slurry, and also when larger volumes are mixed, maintaining these mixing parameters becomes difficult and this results in different levels of energy input/consumption. Furthermore, field equipment capabilities differ from laboratory-based equipment, and consequently, well cement slurries may be mixable in the laboratory (e.g., under API mixing specifications) but fail to mix or become very difficult to mix in the field.

In some aspects of what is described here, a predictive algorithm is used to determine the energy consumption requirements for mixing of well cement slurries in the laboratory. In some implementations, the energy consumption during the process of laboratory mixing of well cement slurries is measured directly, for example, as described in International Application PCT/US2013/067874, filed on Oct. 31, 2013, entitled, "Correlating Energy to Mix Cement Slurry Under Different Mixing Conditions." The predictive algorithm may then be used to make a priori predictions of the energy consumption of a previously-known or a previously-unknown cement slurry. Such an algorithm can help quantify the "mixability" of a well cement slurry based on the energy consumption and save much time and labor in designing well cement slurries for jobs, thereby potentially helping alleviate costs associated with mixing issues in the field.

Figure 1:
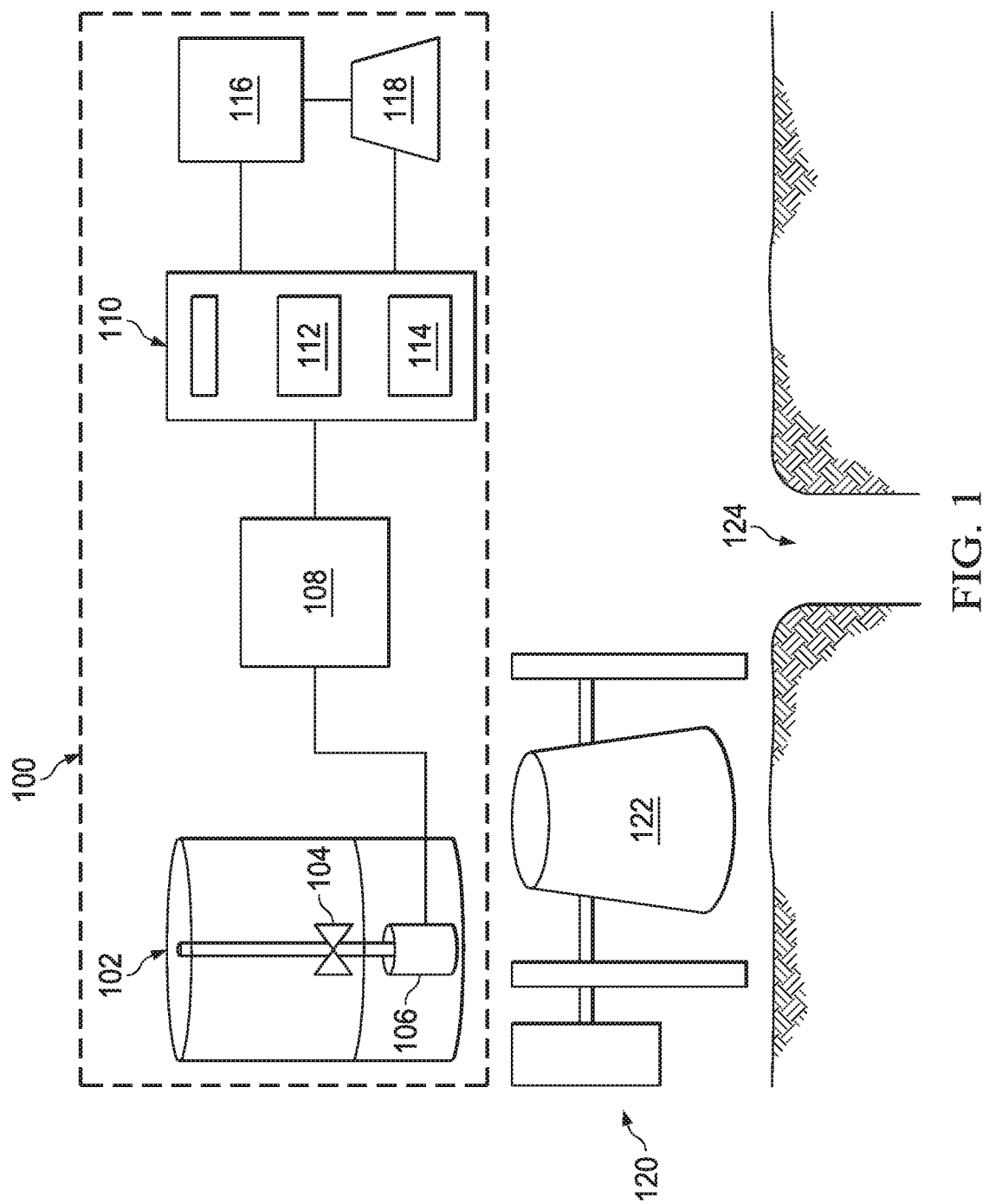
FIG. 1 is a schematic diagram of example systems for mixing a well cement slurry.

FIG. 1 is a schematic diagram of two example systems for mixing a well cement slurry. The two example systems are a laboratory system 100 and a field system 120. The laboratory system 100 includes a laboratory mixer 102 in a laboratory environment where well cement slurries can be tested. The field system 120 includes a field mixer 122 where well cement slurries are prepared for use in a well site 124. The field mixer 122 can be of a different configuration than the laboratory mixer 102. For example, the laboratory mixer 102 can be an electric mixer, and the field mixer 122 can be a hydraulic mixer, a static mixer, an agitator system or other mixer that is different from the laboratory mixer 102.

Some example field mixers include a mixing vessel having a diameter in the range of approximately 24-inches to 36-inches, and operate at an agitation speed of approximately zero to 2,000 rotations per minute (RPM). Some example laboratory mixers include a mixing vessel having a diameter in the range of approximately 6-inches, and operate at an agitation speed of approximately zero to 12,000 rotations per minute (RPM). Other types of mixers can be used to mix a well cement slurry in a laboratory environment, in a field environment, or in another environment (e.g., a Hobart mixer, etc.).

The laboratory mixer 102 can be configured to mix a well cement slurry, for example, under API specifications or other specifications. The laboratory mixer 102 can be an electric mixer that includes, e.g., an impeller 104 connected to a motor 106 to rotate the impeller 104. The laboratory mixer 102 can be connected to a measurement device 108 to directly measure electrical power supplied to the mixer in mixing a specified well cement slurry. In some implementations, the measurement device 108 can be a multimeter connected to the motor 106 to measure parameters to determine the electrical power, e.g., a voltage across the motor 106, a current through the motor 106, other parameters or combinations of them. The laboratory system 100 can also include additional measurement devices, for example, to measure the properties (e.g., mass, density, viscosity, etc.) of the well cement slurry in the mixer.

The measurement device 108 can be connected to a computer system 110 which includes one or more processors 112 and a computer-readable medium 114 storing instructions executable by the one or more processors 112 to analyze data from mixing of the well cement slurry. The computer system 110 can include a computer, e.g., a desktop computer, a laptop computer, a smartphone, a tablet computer, a personal digital assistant (PDA) or other computer. The computer system 110 can be connected to one or more input devices 116 and one or more output devices 118. In some implementations, the computer system 110 can be implemented as hardware or firmware integrated into the measurement device 108. Alternatively, or in addition, the measurement device 108 can be integrated into the computer system 110. In some implementations, data from the measurement device 108 can be manually input into the computer system 110, e.g., using the one or more input devices 116.

Sometimes well cement slurries mix with ease in the laboratory, but pose challenges when mixed using field equipment. Some of the major reasons for the discrepancy between the laboratory and the field mixes may include, but are not limited to (a) inadequate comprehension of power requirements for mixing of well cement slurries in the laboratory, and (b) inaccurate power consumption requirement for mixing well cement slurries under field conditions, as correlated to the power consumption requirements in the laboratory. Existing API mixing specifications followed in the laboratory are unable to help evaluate an order-of-magnitude power consumption requirement of the mixing of complex slurries in the field versus in the laboratory or to help evaluate the "mixability" of well cement slurries in the field vis-à-vis in the laboratory.

Some implementations of the techniques described here can predict power consumption requirements for mixing of a fluid (e.g., well cement slurries and other well system fluids), before actual measurement of the fluid, knowing identified design variables. Then, knowing the power consumption requirements for mixing of previously "easy-to-mix" well cement slurries and "hard-to-mix" well cement slurries, an unknown slurry can be classified as "mixable" or not, based on power consumptions for mixing it in the laboratory. A theoretical consideration for the algorithm is included in the following discussion of the predictive algorithms and related techniques.

Power consumption in a batch mixer can be estimated from the following equation:

$$\frac{P}{V} = \tau_{average} \times \gamma_{average}. \qquad \text{Eqn (1)}$$

Further equations relating to mixing in a batch mixer are as follows:

$$N_P = \frac{\int \frac{P}{\rho(t)N^3D^5}dt}{\int dt}, \qquad \text{Eqn (2)}$$

$$Re = \frac{\int \frac{\rho N D^2}{\mu(t)}dt}{\int dt}. \qquad \text{Eqn (3)}$$

In the equations above, the following variables are used:
$\tau_{average}$=Average Shear Stress in the fluid in the batch mixer (Pa);
$\gamma_{average}$=Average Shear Rate in the fluid in the batch mixer ($s^{-1}$);
P=Power consumed in the batch mixer because of impeller motion (Watt);
$N_P$=Time-average Power Number for the particular impeller used in the laboratory blender/field mixer (dimensionless), following the temporal evolution of density when mixing dry cement blend with mix water. Spatial variations can be accounted for as well, if so deemed necessary;
$\rho$=Homogenous density of the fluid in the batch mixer (kg $m^{-3}$). This would be time-varying, until complete homogeneity is attained (several seconds). A method such as static/dynamic light scattering or other suitable methods might be employed to follow the evolution of this parameter with time;
V=Volume of fluid ($m^3$);
N=Agitation speed ($s^{-1}$);
D=Diameter of the impeller (m);
$\mu$=Apparent viscosity (also referred to as Plastic Viscosity or PV) of non-Newtonian fluid (Pa-s). This would be time-varying, until complete homogeneity is attained (several seconds). A method such as static/dynamic light scattering or other suitable methods might be employed to follow the evolution of this parameter with time, along with using appropriate methods to calculate the viscosities; and
Re=Time-averaged Reynolds Number characterizing the fluid motion in the batch mixer (dimensionless), following the temporal evolution of viscosity when mixing dry cement blend with mix water. Spatial variations can be accounted for as well, in some cases.

Scale-up considerations and power consumption in agitator systems can be analyzed based on the Buckingham pi theorem formulation, considering a dimensional analysis of the various factors that contribute to power consumption:

$$f\left(\frac{D^2N\rho}{\mu}, \frac{DN^2}{g}, \frac{P}{\rho N^3 D^5}, \frac{D}{T}, \frac{D}{Z}, \text{others}\right) = 0. \qquad \text{Eqn (4)}$$

In the equation above, "others" refers to other groups of geometric similarity, and:

g=Universal constant (acceleration due to gravity) (m/s²);
T=Diameter of blender tank (m); and
Z=Ratio of tank diameter to impeller diameter (dimensionless).

Equation (4) above can also be re-written as:

$$N_p = C(Re)^x (Fr)^y \text{(others)} \quad \text{Eqn (5)},$$

where "others" refers to other dimensionless groups of geometric similarity, raised to their respective powers, and Fr refers to the Froude number (characteristic of vortex formation in stirred systems).

Keeping blender geometry and impeller geometry parameters constant (e.g., adhering to the standard WARING® blender recommended for laboratory mixing by API), the above Equation (5) can be written as:

$$N_p = C(Re)^x (Fr)^y \quad \text{Eqn (6)}.$$

This can further be expressed as:

$$\phi = N_p/(Fr)^y = C(Re)^x \quad \text{Eqn (7)},$$

where $\phi$ refers to the power function (characteristic of power consumption for stirring). The contribution of the Froude number (which is relevant for the effects of vortexing and surface aeration in batch mixers) for this instance can be neglected, and y=0. Hence, $$\phi = N_p = C(Re)^x \quad \text{Eqn (8)}$$

Hence, for the mixing of well cement slurries in the laboratory, the power function is the power number for the particular stirred system in consideration. This also indicates that the power number will be a function of the variables that define the Reynolds number of the stirred system. Based on the equations above, an algorithm can be used for evaluating power consumption for laboratory mixing of well cement slurries and other well system fluids.

Figure 2:
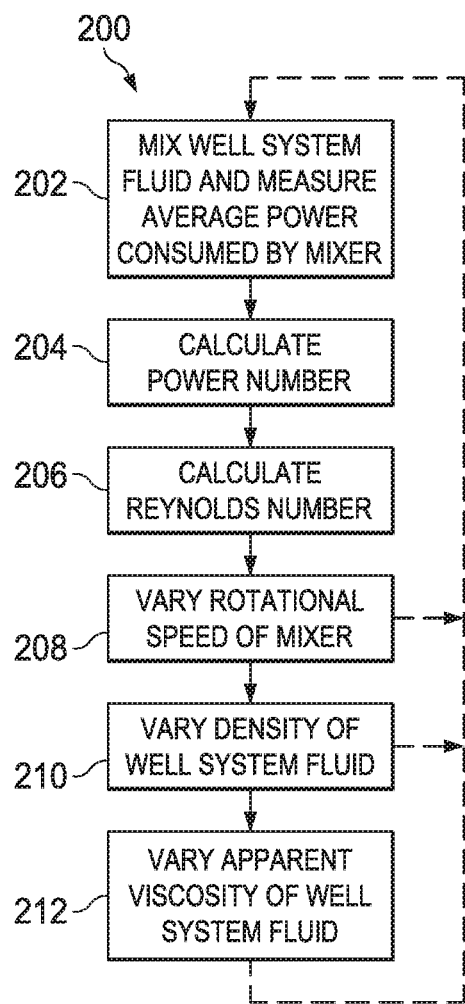
FIG. 2 is flow chart showing an example process for analyzing mixability of well cement slurries.

FIG. 2 is a flowchart of an example process 200 for analyzing mixability of well cement slurries. In some implementations, at least a portion of the process 200 can be implemented by the laboratory mixer 102, the measurement device 108, the computer system 110 or combinations of them. In some implementations, at least a portion of the process 200 can be implemented by the field mixer 122, measurement devices, an operator, or combinations of them.

In some implementations, the process 200 can be scientifically more rigorous, more direct and more portable across laboratories or other settings, for example, as compared to existing techniques (e.g., conventional techniques that are based on the incorporation of approximation and the evaluation of certain constants of approximation). In some implementations, the process 200 provides a quantitative technique to evaluate the mixability of a well cement slurry in the field based on laboratory data, and also an improved method in the scientific evaluation of well system fluid mixability and on the required energy consumption.

Generally, the process 200 can be used with any type of mixer, in a variety of environments and with any type of well system fluid. In the following discussion, an example of an electric mixer mixing well cement slurries in a lab environment is considered. The process 200 can be used in the example application or in other applications to assign a mixability index to a new well system fluid mixture. In some cases, the mixability index can be computed for a variety of fluids to be mixed by the same mixer.

Initially in the process 200, constituents of a well cement slurry are received. The constituents can include a quantity of each well cement slurry component to be mixed, a quantity of water (or other fluid) to be added to mix the multiple components, etc.

At 202, the components of the specified well cement slurry are mixed in a mixer. To do so, respective quantities of components of the well cement slurry (e.g., hydraulic cement, water, additives, or other components) can be added to the mixer. In some implementations, dry additives can also be added to the liquids in the well cement slurry. In one example instance, the motor 106 can be operated to rotate the impeller 104 at a specified speed of mixing and for a specified time of mixing to mix the multiple components of the well cement slurry. In other example instances, the motor 106 can be operated to rotate the impeller 104 at respective (e.g., different or time-varying) speeds of mixing and for respective (e.g., different) times of mixing to mix the multiple components of the well cement slurry.

Also at 202, the average power consumed by the mixer mixing the well cement slurry is measured. The power used by the mixer in mixing the well cement slurry can be measured, for example, as described in International Application PCT/US2013/067874, filed on Oct. 31, 2013, entitled, "Correlating Energy to Mix Cement Slurry Under Different Mixing Conditions," or the power can be measured in another manner. In some examples, a voltage across and a current drawn by the mixer can be directly measured while mixing the well cement slurry. In some implementations, a measurement device (e.g., a multimeter) can be directly connected to the motor of the mixer to measure the voltage across and the current drawn by the motor while mixing. The measurement device can be implemented to obtain multiple measurements of voltage and current, each measurement corresponding to a respective instance of operating the motor at a mixing speed for a mixing time.

In some implementations, the energy to mix the specified well cement slurry can be determined based on the measured voltage and the current. For instance, the measurement device can transmit the measured voltage and current to a data analysis system, which can implement computer operations to determine the electrical power, e.g., as a product of voltage and current. For example, the voltage and current can be measured for a period of time in the laboratory system under the laboratory conditions. The electrical power can be determined as a product of a time-averaged voltage and a time-averaged current. For the multiple instances of operating the motor, the data analysis system can determine multiple values of electrical power, each value being a product of a respective time-averaged voltage and time-averaged current. Upon measuring the electrical power supplied to the mixer, the energy to mix the specified well cement slurry from the measuring can be determined. In some implementations, the energy can be electrical energy determined as a product of electrical power and the time of application of the electrical power. In some examples, the average power consumed by a WARING® blender in the laboratory under a constant-held motor rotational speed (N) is measured.

In some cases, the well cement slurry is completely mixed and homogeneous before measuring the energy consumed by the mixer. In some cases, the well cement slurry is unmixed and non-homogeneous when the energy measurements commence.

At 204, the power number is calculated. For example, knowing the temporal evolution of the density of the slurry design used, one can calculate the power number $N_p$ of this system under this condition, with the help of Equation (2) above. In some cases, the temporal evolution can be neglected.

At 206, the Reynolds number of the fluid in the mixer is calculated. For example, knowing the density and apparent viscosity of the fluid, the size of the impeller and agitation speed of the mixer, and other relevant parameters, Equation (3) above can be used to compute the Reynolds number.

At 208, the rotational speed (N) of the mixer impeller is varied and the operations 202, 204, 206 are repeated for one or more distinct rotational speeds. For example, the rotational speed of the blender motor can be varied to different (e.g., constantly-held, or time-varying) rotational speeds to measure the power consumed by the blender. Thereupon, the variation of the power number $N_p$ of the system with a blender RPM can be measured. Typically, this should generate a function of the form:

$$N_p = f(N) \qquad \text{Eqn (9)}.$$

At 210, the density (ρ) of the well cement slurry is varied, and the operations 202, 204, 206, 208 are repeated for one or more distinct densities. Typically, this should generate a function of the form:

$$N_p = f(N, \rho) \qquad \text{Eqn (10)}.$$

At 212, the apparent viscosity (μ) (also referred to as plastic viscosity or PV) of the well cement slurry is varied, and the operations 202, 204, 206, 208, 210 are repeated for one or more distinct apparent viscosities. Typically, this should generate a function of the form:

$$N_p = f(N, \rho, \mu) \qquad \text{Eqn (11)}$$

For each combination of the variables N, ρ, and μ, the associated Reynolds number Re is calculated at 206 utilizing Equation 3. This can generate a function of the form:

$$N_p = f(Re) \qquad \text{Eqn (12)}$$

A comparison of Eqns (8) and (12) show that the following may be graphed for different values of N, ρ, and μ:

$$N_p = C(Re)^x \qquad \text{Eqn (13)}.$$

Eqn (13) provides of a functional relationship between power number ($N_p$) and Reynolds number (Re), and values for the parameters C and x can be identified based on data points (e.g., the power number values and the Reynolds number values) from each iteration of the operations shown in FIG. 2. For example, the data points can be fitted or otherwise analyzed to compute particular values for the parameters C and x. In some cases, the data points are fitted using least-squares regression or another type of fitting technique.

In some cases, the parameters C and x are constants. The variation of the parameters would not be expected to be large for a particular fluid system, e.g., well cement slurry systems. Hence, based on the particulars of the speed of agitation, density and apparent viscosity of the slurry to be mixed, an operating value of the power number $N_p$ may be pre-evaluated based on the graphical form of Eqn (13) from previously conducted experiments. Then, based on the value of the power number NM, and using Eqn (2), an operating value of the power required for mixing the slurry contents at any pre-determined conditions of N, ρ, and μ may be evaluated, thereby giving an order-of-magnitude estimate of the energy requirements for mixing of an unknown well cement slurry. This characteristic will be useful, for example, when pre-determining the "mixability" of the well cement slurry through a comparison of the predicted energy requirements with previously mixed "easy to mix" and "hard to mix" slurries, and in other contexts. This process can save time, labor and money, for example, when dealing with difficult to mix slurries.

Figure 3:
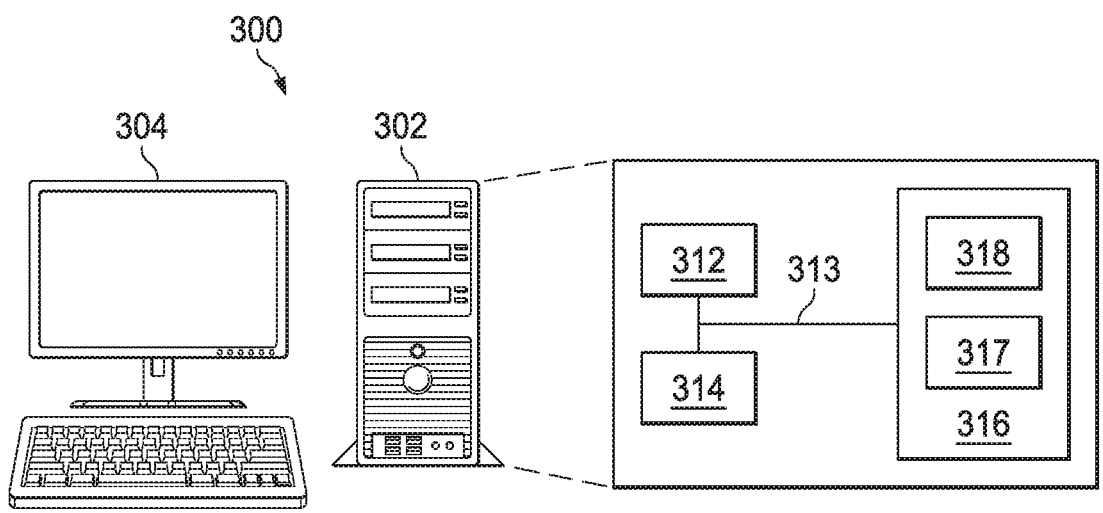
FIG. 3 is a schematic diagram of an example data analysis system.

FIG. 3 is a schematic diagram of an example data analysis system 300 that includes a computer system 302 and a display device 304. The data analysis system 300 can be located at a data-processing center, a computing facility, or another location. The example data analysis system 300 can communicate with (e.g., send data to or receive data from) a mixing system. For example, the data analysis system 300 may receive data from either of the example systems in FIG. 1 or another type of mixing system. In some examples, all or part of the data analysis system 300 may be included with or embedded in a mixing system. The data analysis system 300 or any of its components can be located with or apart from a mixing system.

In some implementations, the data analysis system 300 can include or be implemented on various types of devices, including, but not limited to, personal computer systems, desktop computer systems, laptops, mainframe computer systems, handheld computer systems, application servers, computer clusters, distributed computing systems, workstations, notebooks, tablets, storage devices, or another type of computing system or device.

The example display device 304 can produce a visual output. The display device 304 can include a computer monitor (e.g., LCD screen), a projector, a printer, a touch-screen device, a plotter, or a combination of one or more of these. In some instances, the display device 304 displays data obtained by a mixing system, plots of data obtained by analyzing mixing data, or other types of information.

As shown in the schematic diagram in FIG. 3, the example computer system 302 includes a memory 316, a processor 314, and input/output controllers 312 communicably coupled by a bus 313. A computing system can include additional or different features, and the components can be arranged as shown or in another manner. The memory 316 can include, for example, a random access memory (RAM), a storage device (e.g., a writable read-only memory (ROM) or others), a hard disk, or another type of storage medium. The computer system 302 can be preprogrammed or it can be programmed (and reprogrammed) by loading a program from another source (e.g., from a CD-ROM, from another computer device through a data network, or in another manner).

In some examples, the input/output controllers 312 are coupled to input/output devices (e.g., a monitor, a mouse, a keyboard, or other input/output devices) and to a network. The input/output devices can communicate data in analog or digital form over a serial link, a wireless link (e.g., infrared, radio frequency, or others), a parallel link, or another type of link. The network can include any type of communication channel, connector, data communication network, or other link. For example, the network can include a wireless or a wired network, a Local Area Network (LAN), a Wide Area Network (WAN), a private network, a public network (such as the Internet), a WiFi network, a network that includes a satellite link, or another type of data communication network.

The memory 316 can store instructions (e.g., computer code) associated with an operating system, computer applications, and other resources. The memory 316 can also store application data and data objects that can be interpreted by one or more applications or virtual machines running on the computer system 302. As shown in FIG. 3, the example memory 316 includes data 318 and applications 317. The data 318 can include well cement slurry data, fluid data, mixer data, or other types of data. The applications 317 can include data analysis software, simulation software, or other types of applications. In some implementations, a memory of a computing device includes additional or different data, application, models, or other information.

The processor 314 can execute instructions, for example, to generate output data based on data inputs. For example, the processor 314 can run the applications 317 by executing or interpreting the software, scripts, programs, functions, executables, or other modules contained in the applications 317. The input data received by the processor 314 or the output data generated by the processor 314 can include any of the mixing data, cement slurry data, parameter data, or other information.

The example well cement slurries described above may directly or indirectly affect one or more components or pieces of equipment associated with the preparation, delivery, recapture, recycling, reuse, or disposal of the disclosed binder compositions. For example, the well cement slurries may directly or indirectly affect one or more mixers, related mixing equipment, mud pits, storage facilities or units, composition separators, heat exchangers, sensors, gauges, pumps, compressors, and the like used to generate, store, monitor, regulate, or recondition the well cement slurries. The well cement slurries may also directly or indirectly affect any transport or delivery equipment used to convey the binder compositions to a well site or downhole such as, for example, any transport vessels, conduits, pipelines, trucks, tubulars, or pipes used to compositionally move the well cement slurries from one location to another, any pumps, compressors, or motors (e.g., topside or downhole) used to drive the well cement slurries into motion, any valves or related joints used to regulate the pressure or flow rate of the well cement slurries, and any sensors (i.e., pressure and temperature), gauges, or combinations thereof, and the like. The well cement slurries may also directly or indirectly affect the various downhole equipment and tools that may come into contact with the cement compositions/ additives such as, for example, wellbore casing, wellbore liner, completion string, insert strings, drill string, coiled tubing, slickline, wireline, drill pipe, drill collars, mud motors, downhole motors or pumps, cement pumps, surface-mounted motors or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like.

Figure 4:
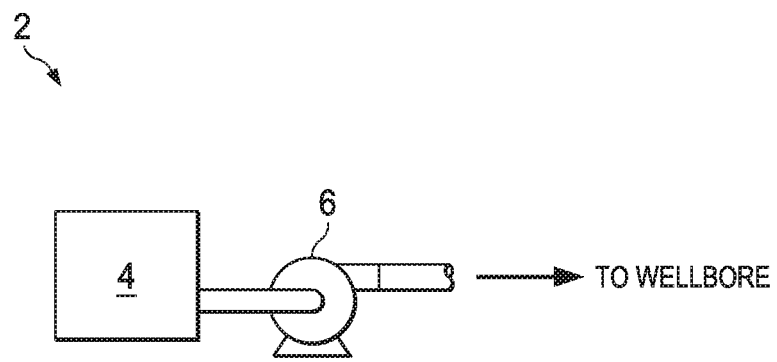
FIG. 4 illustrates a system for preparation and delivery of a cement composition to a wellbore.

Referring now to FIG. 4, a system that may be used in the preparation of a cement composition will now be described. FIG. 4 illustrates a system 2 for preparation of a cement composition and delivery to a wellbore. As shown, the cement composition may be mixed in mixing equipment 4, such as a jet mixer, re-circulating mixer, or a batch mixer, for example, and then pumped via pumping equipment 6 to the wellbore. In some instances, the mixing equipment 4 and the pumping equipment 6 may be disposed on one or more cement trucks. In some instances, a jet mixer may be used, for example, to continuously mix the composition, including water, as it is being pumped to the wellbore.

Figure 5A:
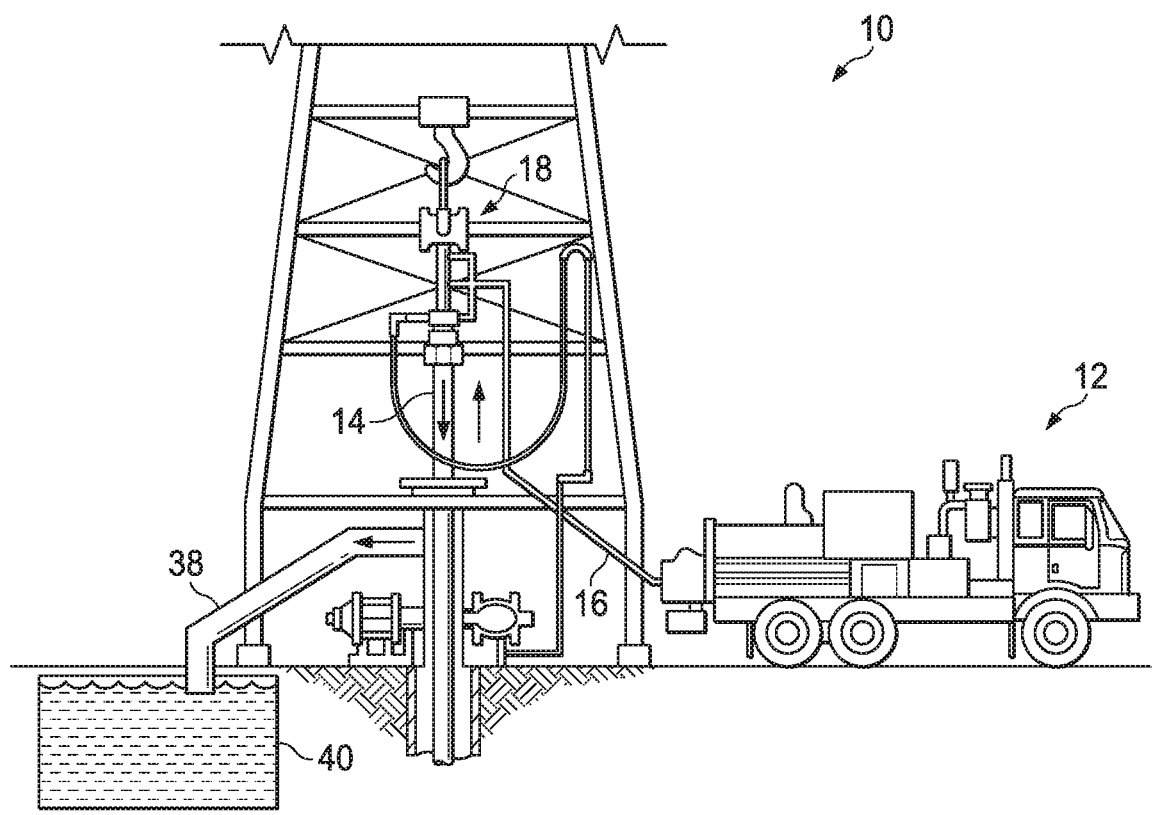
FIG. 5A illustrates surface equipment that may be used in placement of a cement composition in a wellbore.

An example technique and system for placing a cement composition into a subterranean formation will now be described with reference to FIGS. 5A and 5B. FIG. 5A illustrates surface equipment 10 that may be used in placement of a cement composition. While FIG. 5A generally depicts a land-based operation, the principles are applicable to subsea operations that employ floating or sea-based platforms and rigs. As illustrated by FIG. 5A, the surface equipment 10 may include a cementing unit 12, which may include one or more cement trucks. The cementing unit 12 may include mixing equipment 4 and pumping equipment 6 (e.g., FIG. 4). The cementing unit 12 may pump a cement composition 14 through a feed pipe 16 and to a cementing head 18 which conveys the cement composition 14 downhole.

Figure 5B:
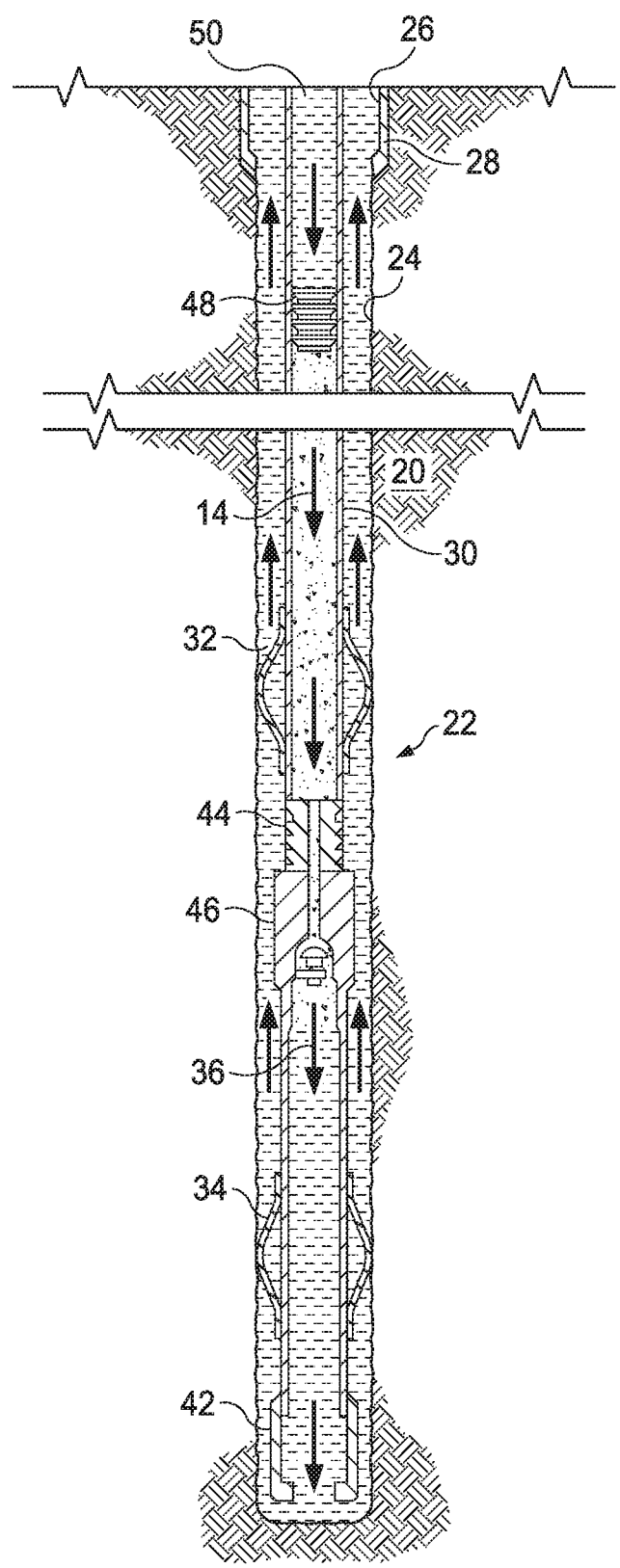
FIG. 5B illustrates placement of a cement composition into a wellbore annulus.

Turning now to FIG. 5B, the cement composition 14 may be placed into a subterranean formation 20. As illustrated, a wellbore 22 may be drilled into the subterranean formation 20. While wellbore 22 is shown extending generally vertically into the subterranean formation 20, wellbores may extend at an angle through the subterranean formation 20, such as horizontal and slanted wellbores. As illustrated, the wellbore 22 comprises walls 24. In the example shown, a surface casing 26 has been inserted into the wellbore 22. The surface casing 26 may be cemented to the walls 24 of the wellbore 22 by cement sheath 28. One or more additional conduits (e.g., intermediate casing, production casing, liners, etc.) shown here as casing 30 may also be disposed in the wellbore 22. As illustrated, there is a wellbore annulus 32 formed between the casing 30 and the walls 24 of the wellbore 22 or the surface casing 26. One or more centralizers 34 may be attached to the casing 30, for example, to centralize the casing 30 in the wellbore 22 prior to and during the cementing operation.

With continued reference to FIG. 5B, the cement composition 14 may be pumped down the interior of the casing 30. The cement composition 14 may be allowed to flow down the interior of the casing 30 through the casing shoe 42 at the bottom of the casing 30 and up around the casing 30 into the wellbore annulus 32. The cement composition 14 may be allowed to set in the wellbore annulus 32, for example, to form a cement sheath that supports and positions the casing 30 in the wellbore 22. Other techniques may also be utilized for introduction of the cement composition 14. By way of example, reverse circulation techniques may be used that include introducing the cement composition 14 into the subterranean formation 20 by way of the wellbore annulus 32 instead of through the casing 30.

As it is introduced, the cement composition 14 may displace other fluids 36, such as drilling fluids or spacer fluids, that may be present in the interior of the casing 30 or the wellbore annulus 32. At least a portion of the displaced fluids 36 may exit the wellbore annulus 32 via a flow line 38 and be deposited, for example, in one or more retention pits 40 (e.g., a mud pit), as shown on FIG. 5A. Referring again to FIG. 5B, a bottom plug 44 may be introduced into the wellbore 22 ahead of the cement composition 14, for example, to separate the cement composition 14 from the fluids 36 that may be inside the casing 30 prior to cementing. After the bottom plug 44 reaches the landing collar 46, a diaphragm or other suitable device ruptures to allow the cement composition 14 through the bottom plug 44. In FIG. 5B, the bottom plug 44 is shown on the landing collar 46. In the illustrated example, a top plug 48 may be introduced into the wellbore 22 behind the cement composition 14. The top plug 48 may separate the cement composition 14 from a displacement fluid 50 and also push the cement composition 14 through the bottom plug 44.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer storage medium for execution by, or to control the operation of, data-processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data-processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read-only memory or a random-access memory or both. A computer can include a processor that performs actions in accordance with instructions, and one or more memory devices that store the instructions and data. A computer may also include, or be operatively coupled to receive data from or transfer data to, or both, one or more mass storage devices for storing data, e.g., magnetic disks, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. In some cases, the processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

In a general aspect, this specification describes methods and systems for analyzing a well system fluid, such as, for example, a well cement slurry.

In some aspects, a method of analyzing a well cement slurry includes mixing a well cement slurry in a mixer (e.g., a laboratory mixer, a field mixer, etc.) under a plurality of conditions. The plurality of conditions correspond to a plurality of distinct Reynolds number values for the well cement slurry in the mixer. For example, each condition can correspond to a distinct value of one or more of the following variables: the rotational speed (N) of the impeller that agitates the well cement slurry in the mixer, the density ($\rho$) of the well cement slurry, the apparent viscosity ($\mu$) of the well cement slurry, and possibly others. Power number values associated with mixing the well cement slurry in the mixer under the plurality of conditions are identified. Each power number value is based on measurements indicating an amount of energy used to mix the well cement slurry under a respective one of the plurality of conditions. Values for parameters of a functional relationship between power number ($N_p$) and Reynolds number (Re) are identified based on the power number values and the Reynolds number values for the plurality of conditions.

In some implementations, the functional relationship comprises $N_p=C(Re)^x$, and identifying values for the parameters of the functional relationship comprises identifying values for C and x. In some cases, the functional relationship and the identified values for the parameters can be used to compute a predicted power number value associated with mixing the well cement slurry under another distinct condition. Here, the other distinct condition is different from the plurality of conditions that were used to compute the values of the parameters. For example, the other distinct condition can correspond to a different value of one or more of the following variables: the rotational speed (N) of the impeller that agitates the well cement slurry in the mixer, the density ($\rho$) of the well cement slurry, the apparent viscosity ($\mu$) of the well cement slurry, and possibly others.

In some cases, the functional relationship and the identified values for the parameters can be used to compute a predicted power number value associated with mixing another well cement slurry, and the predicted power number can be used to estimate the energy to mix the other well cement slurry. In some cases, the functional relationship and the identified values for the parameters can be used to determine a mixability index associated with mixing the same or another well cement slurry. The mixability index can be a quantitative, objective index that is related to the power number or another quantity.

A number of examples have been described. Various modifications can be made without departing from the scope of the present disclosure. Accordingly, other embodiments are within the scope of the following claims.

What is claimed is:

1. A system for analyzing well cement slurry mixing, the system comprising:
   a mixer for mixing a dry cement blend with mix water to form a well cement slurry under a plurality of conditions, the plurality of conditions corresponding to a plurality of distinct Reynolds number values for the well cement slurry in the mixer;
   a measurement device to measure an amount of energy used to mix the well cement slurry in the mixer; and
   a data analysis system comprising:
      a data-processing apparatus; and
      memory storing computer-readable instructions that, when executed by the data-processing apparatus, cause the data-processing apparatus to perform operations comprising:
         identifying power number values associated with the mixing of the well cement slurry under the plurality of conditions, each power number value based on the amount of energy used to mix the well cement slurry under a respective one of the plurality of conditions; and
         identifying values for parameters of a functional relationship between power number and Reynolds number based on the power number values and the Reynolds number values for the plurality of conditions, wherein:
            the power number is dependent upon a time-varying fluid density measured from when the dry cement blend is mixed with the mix water until the well cement slurry is homogenous as confirmed by static or dynamic light scattering,
            the Reynolds number is dependent upon a time-varying apparent fluid viscosity measured from when the dry cement blend is mixed with the mix water until the well cement slurry is homogenous as confirmed by static or dynamic light scattering, and
            the functional relationship with the identified values for the parameters is used to determine a mixability index associated with the mixing to form another well cement slurry.

2. The system of claim 1, wherein the functional relationship comprises $N_p=C(Re)^x$, and identifying values for the parameters of the functional relationship comprises identifying values for C and x, where C and x are constants $N_p$ represents the power number, and Re represents the Reynolds number.

3. The system of claim 1, wherein the mixer comprises an impeller that agitates the well cement slurry, at least a subset of the plurality of conditions correspond to a plurality of distinct rotational speeds of the impeller, at least a subset of the plurality of conditions correspond to a plurality of distinct densities of the well cement slurry, and at least a subset of the plurality of conditions correspond to a plurality of distinct viscosities of the well cement slurry.

4. The system of claim 1, the operations further comprising:
   using the functional relationship and the identified values for the parameters to compute a predicted power number value associated with mixing the well cement slurry under another distinct condition; and
   using the predicted power number value to estimate the energy to mix the well cement slurry under the other distinct condition.

5. The system of claim 1, the operations further comprising using the functional relationship with the identified values for the parameters to compute a predicted power number value associated with mixing the other well cement slurry.

6. The system of claim 5, the operations further comprising using the predicted power number value to estimate the energy to mix the other well cement slurry.

7. The system of claim 1, the operations further comprising using the functional relationship with the identified values for the parameters to determine a mixability index associated with mixing another well cement slurry.

8. The system of claim 1, further comprising a pump to communicate the well cement slurry into a wellbore in a subterranean region.

9. The system of claim 1, wherein the mixer to mix the dry cement blend with the mix water to form the well cement slurry includes one or more of a jet mixer, re-circulating mixer, or a batch mixer.

10. The system of claim 9, wherein the jet mixer continuously mixes the well cement slurry, including water, as it is being pumped to a wellbore in a subterranean region.

* * * * *